United States Patent
Collazo et al.

(10) Patent No.: US 10,926,051 B2
(45) Date of Patent: Feb. 23, 2021

(54) RESPIRATORY INTERFACE

(71) Applicant: InnoMed Healthscience, Inc., Coconut Creek, FL (US)

(72) Inventors: Louis Javier Collazo, Pompano Beach, FL (US); Angelo Caruso, Boca Raton, FL (US); Shara Hernandez, Davie, FL (US); Bruce Sher, North Palm Beach, FL (US)

(73) Assignee: InnoMed Healthscience, Inc., Coconut Creek, FL (US)

( * ) Notice: Subject to any disclaimer, the term of this patent is extended or adjusted under 35 U.S.C. 154(b) by 259 days.

(21) Appl. No.: 14/034,162

(22) Filed: Sep. 23, 2013

(65) Prior Publication Data

US 2014/0083419 A1 Mar. 27, 2014

Related U.S. Application Data

(60) Provisional application No. 61/704,126, filed on Sep. 21, 2012.

(51) Int. Cl.
*A61M 15/08* (2006.01)
*A61M 16/06* (2006.01)
*A61M 16/20* (2006.01)

(52) U.S. Cl.
CPC ...... *A61M 16/0666* (2013.01); *A61M 16/208* (2013.01); *A61M 15/085* (2014.02); *A61M 2210/0618* (2013.01)

(58) Field of Classification Search
CPC ............ A61M 15/085; A61M 16/0051; A61M 16/0666; A61M 16/20; A61M 16/208; A61M 16/0688; A61M 16/0866; A61M 2210/0618; A61M 15/002; A61M 15/08; A61M 16/00; A61M 16/0063; A61M 16/0066; A61M 16/0069; A61M 16/0075; A61M 16/0493; A61M 16/06; A61M 16/0605; A61M 16/0611; A61M 16/0616;
(Continued)

(56) References Cited

U.S. PATENT DOCUMENTS 2,534,636 A * 12/1950 Stirn ..................... A61M 13/00
128/203.15
2,642,063 A * 6/1953 Brown .............. A61M 15/0016
128/203.15
(Continued)

FOREIGN PATENT DOCUMENTS

WO WO 2010139014 A1 * 12/2010 ............ A61M 16/06

OTHER PUBLICATIONS

International Search and Written Opinion dated Dec. 26, 2014 from corresponding International Application No. PCT/US2014/055739; 13 pgs.

*Primary Examiner* — Annette Dixon
(74) *Attorney, Agent, or Firm* — Maier & Maier, PLLC

(57) ABSTRACT

Embodiments disclosed herein relate to respiratory interfaces for use in treating various respiratory issues including, but not limited to, sleep disorder breathing (e.g. snoring, sleep apnea), and in other forms of assisted and unassisted respiration. Embodiments disclosed herein further relate to nasal prongs, flanges and valves for use with respiratory interfaces. Embodiments disclosed herein further relate to evaluating patient compliance with a respiratory interface and harvesting energy for the respiratory.

22 Claims, 4 Drawing Sheets

(58) Field of Classification Search
CPC .......... A61M 16/0622; A61M 16/0633; A61M 16/0644; A61M 16/0672; A61M 16/0677; A61M 16/0683; A61M 16/0694; A61M 16/0816; A61F 5/08; A61F 5/56; Y10T 29/49826; Y10T 156/1064
USPC .......... 128/200.24, 200.26, 203.22, 204.18, 128/205.24, 205.25, 206.11, 206.13, 128/206.21, 206.24, 207.11, 207.13, 128/207.18, 848; 600/529, 533, 537
See application file for complete search history.

(56) References Cited

U.S. PATENT DOCUMENTS

| | | | | |
|---|---|---|---|---|
| 3,373,735 | A * | 3/1968 | Gallagher | A61B 5/14539 600/581 |
| 4,155,358 | A * | 5/1979 | McAllister | A62B 18/088 128/202.22 |
| 4,267,831 | A * | 5/1981 | Aguilar | A61M 15/085 128/203.14 |
| 4,488,547 | A * | 12/1984 | Mason | A41D 13/11 116/206 |
| 5,927,951 | A * | 7/1999 | Tamari | A61M 1/3639 417/476 |
| 6,349,724 | B1 * | 2/2002 | Burton | A61M 16/0057 128/204.18 |
| 6,478,026 | B1 * | 11/2002 | Wood | A61M 16/0666 128/207.13 |
| 7,559,327 | B2 | 7/2009 | Hernandez | A61M 16/06 128/203.22 |
| 9,095,673 | B2 * | 8/2015 | Barlow | A61M 16/06 |
| 9,132,250 | B2 * | 9/2015 | Allum | A61M 16/00 |
| 2002/0092527 | A1 | 7/2002 | Wood | |
| 2003/0086825 | A1 * | 5/2003 | Brennan | G01N 31/223 422/83 |
| 2005/0010125 | A1 * | 1/2005 | Joy | A61B 5/0816 600/529 |
| 2005/0199245 | A1 * | 9/2005 | Brennan | G01N 31/223 128/207.18 |
| 2006/0180149 | A1 | 8/2006 | Matarasso | |
| 2006/0266361 | A1 | 11/2006 | Hernandez | |
| 2007/0277832 | A1 * | 12/2007 | Doshi | A61M 15/08 128/207.18 |
| 2008/0023007 | A1 * | 1/2008 | Dolezal | A62B 23/06 128/206.11 |
| 2008/0221470 | A1 * | 9/2008 | Sather | A61B 5/08 600/533 |
| 2009/0007919 | A1 * | 1/2009 | Dolezal | A61M 15/08 128/206.11 |
| 2009/0241965 | A1 * | 10/2009 | Sather | A61F 5/56 128/207.18 |
| 2009/0308398 | A1 * | 12/2009 | Ferdinand | A61M 15/08 128/207.18 |
| 2011/0108041 | A1 * | 5/2011 | Sather | A61M 15/08 128/848 |
| 2011/0214676 | A1 * | 9/2011 | Allum | A61M 16/00 128/207.18 |
| 2011/0218451 | A1 * | 9/2011 | Lai | A61F 5/56 600/533 |
| 2011/0232646 | A1 | 9/2011 | Ho et al. | |
| 2011/0290256 | A1 * | 12/2011 | Sather | A61F 5/08 128/207.18 |
| 2012/0067349 | A1 * | 3/2012 | Barlow | A61M 16/06 128/205.25 |
| 2013/0019870 | A1 | 1/2013 | Collazo et al. | |

* cited by examiner

RESPIRATORY INTERFACE

This application claims priority to U.S. Provisional Application No. 61/704,126, filed Sep. 21, 2012 and entitled RESPIRATORY INTERFACE, the entire contents of which are hereby incorporated by reference in its entirety.

BACKGROUND

Respiratory interfaces are used for various applications, such as for the treatment of snoring. Another such application involves current treatments for sleep apnea. Sleep apnea is a common sleep disorder characterized by sustained pauses in breathing during sleep. The disorder occurs in both infants and adults. Each episode, known as an apnea, can last more than ten seconds and results in blood oxygen desaturation. A clinical diagnosis of sleep apnea is defined as five or more episodes per hour. There are three types of sleep apnea: central, obstructive, and complex.

Obstructive sleep apnea (OSA) constitutes the most common form of sleep apnea. OSA is a medical condition that includes repeated, prolonged episodes of cessation of breathing during sleep. During a period of wakefulness, the muscles of the upper part of the throat passage of an individual keep the passage open, thereby permitting an adequate amount of air (which contains oxygen) to flow to the lungs. During sleep, the throat passage narrows due to relaxation of the muscles. In individuals having a normal sized throat passage, the narrowed throat passage remains open enough to permit a sufficient level of oxygen to flow into the lungs. However, in individuals with smaller sized throat passages, the narrowed throat passage prohibits adequate amounts of oxygen to flow into the lungs.

In addition, an obstruction, such as a relatively large tongue, an occlusion in the upper respiratory track or an odd-shaped plate can also prohibit a sufficient amount of oxygen to flow to the lungs—thus also resulting in OSA. OSA can result in a variety of medical conditions including daytime drowsiness, headache, weight gain or loss, limited attention span, memory loss, poor judgment, personality changes, lethargy, inability to maintain concentration and/or depression.

Other medical conditions can also prevent individuals, including adults and infants, from receiving an adequate amount of oxygen to the lungs. For example, an infant who is born prematurely can have lungs that are not developed to an extent necessary to receive adequate amounts of oxygen. Further, prior to, during, and/or subsequent to certain medical procedures and/or medical treatments, an individual can be unable to receive an adequate amount of oxygen. Under these circumstances, it is known to use a ventilation interface to apply a positive pressure to the throat of the individual, thereby permitting an adequate amount of oxygen to flow into the lungs.

In known ventilation interfaces, oxygen and/or room air containing oxygen is delivered through the mouth and/or nose of the individual. The most common form of positive pressure treatment for OSA is use of a continuous positive airway pressure (CPAP) device. A CPAP device forces a pressurized breathable gas into the patient's respiratory track and allows air to pass the obstruction(s) and/or occlusion(s). Other forms of positive pressure delivery exist, such as bi-Level positive airway pressure (BiPAP) in which a relatively higher positive pressure is maintained during inspiration and a relatively lower positive pressure is maintained during expiration, and intermittent mechanical positive pressure ventilation (IPPV) in which a positive pressure is applied when apnea is sensed (i.e., the positive airway pressure is applied intermittently or non-continuously). With all these types of therapy, a positive pressure device (i.e., flow generator) connects via a ventilation tube to a ventilation interface. The interface connects to either the patient's nose, mouth or both orifices.

Various interfaces have been developed for positive pressure, and more specifically positive airway pressure (PAP) therapy. These include various shaped full-face masks, nasal masks, nasal prong masks, oral masks and hybrid masks (i.e., those masks that combine masks such as having an oral cavity with nasal prongs). Nasal prongs offer one popular form of interface for use with PAP therapy because they are relatively small, less bulky and more comfortable for many patients to wear for long periods of time.

Nasal prongs can generally be separated into two types: nasal pillows and nasal inserts. Nasal pillows typically abut against the openings of a patient's nares when in use and may not be inserted substantially within the nasal passages. Nasal inserts are typically positioned within the nasal passages of a patient and may or may not abut against the nasal openings. Embodiments and the principles thereof are contemplated for any nasal prong and the like, as will be readily recognized by one having ordinary skill in the art. Nevertheless, for illustrative purposes in a non-limiting manner, exemplary embodiments are described below in reference to nasal inserts.

SUMMARY

Embodiments disclosed herein relate to respiratory interfaces for use in treating various respiratory issues including, but not limited to, sleep disorder breathing (e.g. snoring, sleep apnea), and in other forms of assisted and unassisted respiration. Embodiments disclosed herein further relate to nasal prongs, flanges and valves for use with respiratory interfaces. Embodiments disclosed herein further relate to evaluating patient compliance with a respiratory interface and harvesting energy for the respiratory interface.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1A:
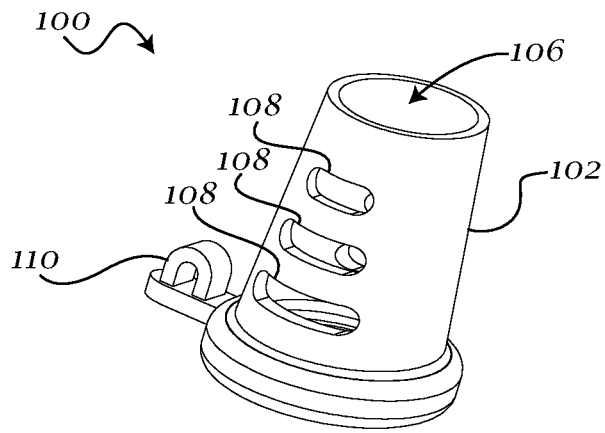
FIGS. 1A-1B illustrate an exemplary embodiment of a nasal insert for a respiratory interface.
Figure 1B:
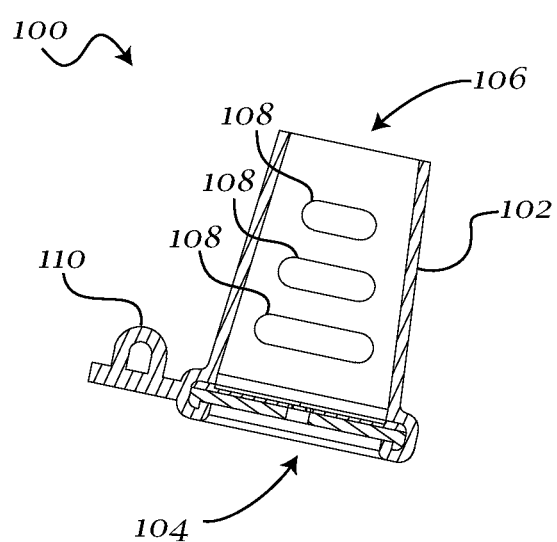

FIGS. 1A-1B illustrate an exemplary embodiment of a nasal insert 100 for a respiratory interface. The nasal insert may include a hollow body 102, an inlet aperture 104 for allowing gas to enter hollow body 102, and a nasal aperture 106 for allowing gas to exit hollow body 102 toward the patient. The nasal insert 100 may have a generally oval shape to facilitate conforming to the shape of the patient's nostril; however, other regular or irregular shapes may be provided. In some exemplary embodiments, a nasal interface can have a single nasal insert 100, as shown in FIGS. 1A-1B. In other exemplary embodiments, a nasal interface can have two nasal inserts 100 as described further below. In some exemplary embodiments, the two nasal inserts 100 may be provided separately. In other exemplary embodiments, the two nasal inserts 100 may be connected, as described further below.

Nasal insert 100 can have at least one weight-reducing structure 108. The weight reducing structures 108 can include indentations or apertures, such as slots, perforations, and like openings that may function to reduce the weight or structure of the nasal insert. The weight reducing structures 108 may be provided in any number, orientation, or combination. In use, nasal insert can function to open the nasal passage to improve airflow and reduce resistance.

Nasal insert 100 can be inserted into the patient's nostril and may form a seal therewith. The fit between nasal insert 100 and the nostril may be sufficient to retain a portion of the nasal insert within a portion of the nostril. In some exemplary embodiments, nasal insert 100 can act as a stent and can compensate for or correct a deviated septum.

In some exemplary embodiments, the nasal insert may have a connection area 110. Connection area 110 may be utilized to connect a headgear (e.g. a strap or the like) to the nasal insert to facilitate supporting the nasal insert 100 as well as creating and/or assisting the seal. In other exemplary embodiments, a headgear could be formed integrally with the respiratory interface having at least one nasal insert 100. Connection area 110 may also be utilized to connect a chin strap to support the interface or limit a patient's ability to open the mouth. In other exemplary embodiments, a chin-strap could be formed integrally with the respiratory interface having at least one nasal insert 100. Furthermore, in some exemplary embodiments, a chin strap or chin flap may be attached to any of the invention embodiments to facilitate keeping the mouth of the patient closed.

Figure 2A:
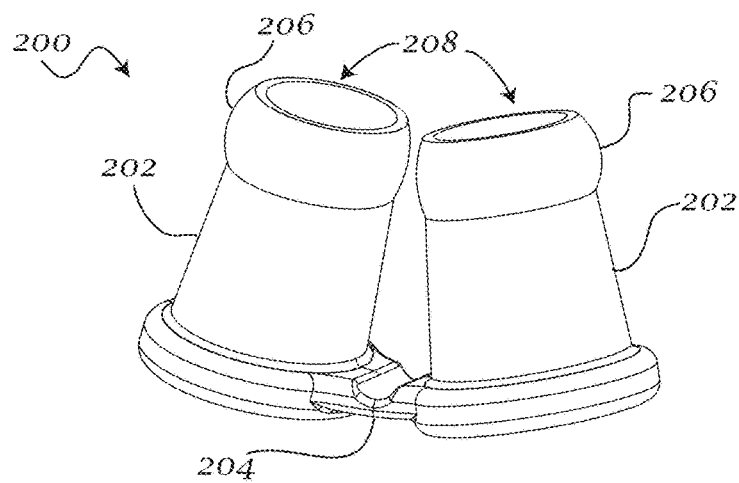
FIGS. 2A-2E illustrate another exemplary embodiment of a respiratory interface and nasal inserts for a respiratory interface.

FIG. 2A illustrates an exemplary embodiment of a respiratory interface 200 having a pair of nasal inserts 202 that may be joined by a connecting member 204. Connecting member 204 can be provided as a separate component or could be formed integrally with nasal inserts 202. Connecting member 204 can have a rectangular cross-section, a circular cross-section, or any other cross-section. Each nasal insert 202 may have a flange 206 on the end having a nasal aperture 208. An exemplary nasal insert with a flange is described in U.S. patent application Ser. No. 10/044,925, filed Jan. 15, 2002, now issued as U.S. Pat. No. 6,595,215, which is hereby incorporated by reference in its entirety.

During use, nasal insert 202 may be retained by flange 206, by the flexibility and resiliency of nasal insert 202 and/or flange 206, or by a combination thereof. In some exemplary embodiments, flange 206 may be in the form of a bead or a thin wiping detail and may facilitate sealing within the nostril. In some exemplary embodiments, flange 206 may be detachably coupled to the nasal insert.

Figure 2B:
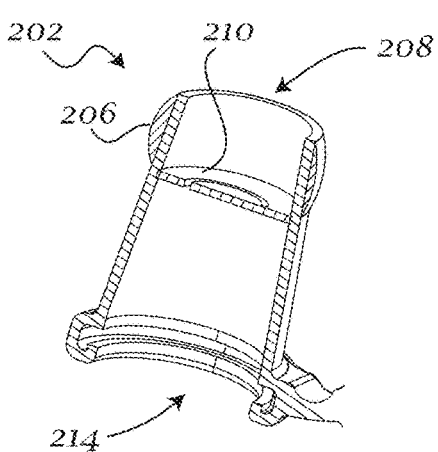
Figure 2C:
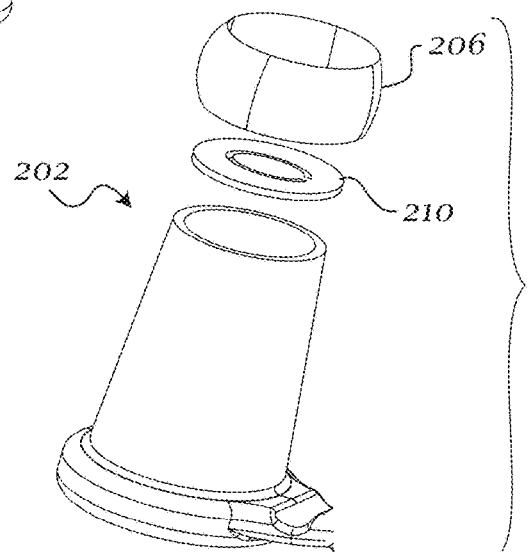

In some exemplary embodiments, nasal insert 202 may further include a valve 210. FIGS. 2B-2C show an exemplary embodiment of a valve 210 located near the nasal aperture 208 of the nasal insert. In this location, the distance between the valve and the nasal aperture may be minimized, thereby facilitating the creation of a smaller deadspace volume. The air that is exhaled by the patient can be trapped in this deadspace. Valve 210 may formed integrally with the nasal insert or may be assembled to the nasal insert.

Figure 2D:
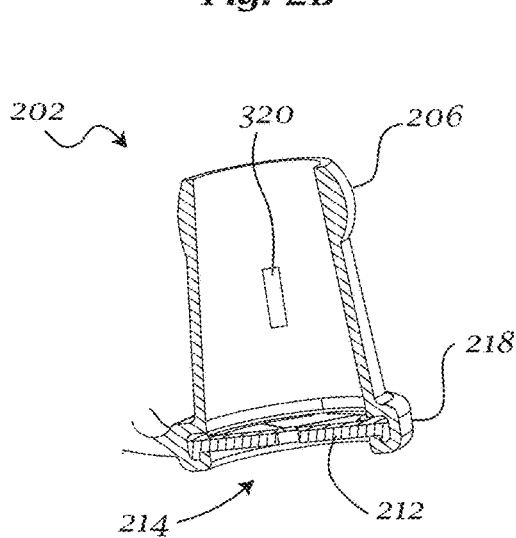
Figure 2E:
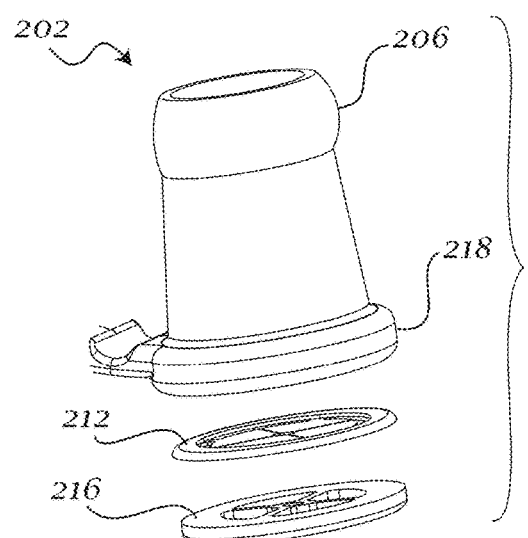

FIGS. 2D-2E show an exemplary embodiment of a valve 212 located near the inlet aperture 214 of the nasal insert. Valve 212 may be formed integrally with the nasal insert or may be assembled to the nasal insert. Each of valves 210 and 212 may be assembled between the nasal insert 202 and a second component, such as, for example, a flange 206 or an inlet aperture cover 216, respectively. In some exemplary embodiments, valve 212 may be attached to an inlet aperture cover 216 by any desired coupling, such as, for example, by assembly or by overmolding. The inlet aperture cover 216 may then be coupled to the nasal insert 202, for example at a valve receptacle 218.

Figure 3A:
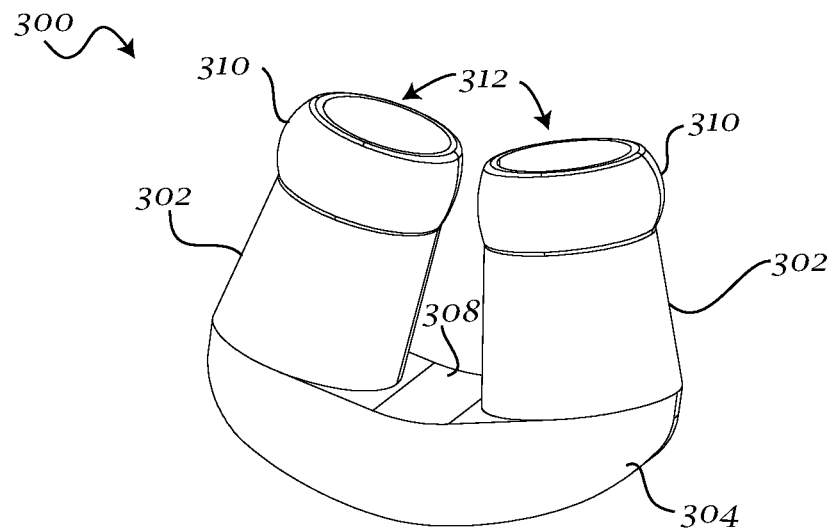
FIGS. 3A-3B illustrate another exemplary embodiment of a respiratory interface.
Figure 3B:
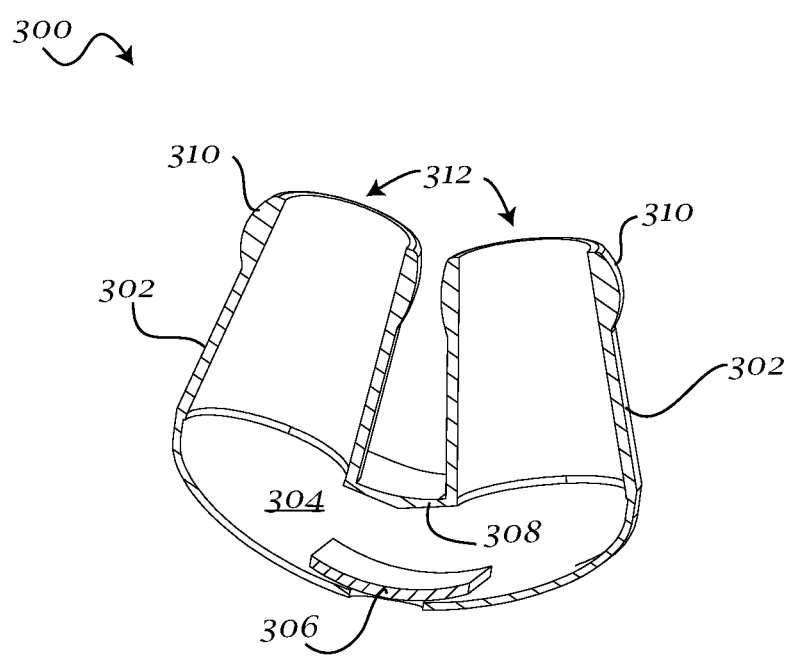

FIGS. 3A-3B illustrate another exemplary embodiment of a respiratory interface 300. Respiratory interface 300 can include a pair of nasal inserts 302 coupled to and in communication with a chamber 304. Chamber 304 may be hollow and may be adapted to reduce deadspace, for example by constructing chamber 304 to be substantially small. In some exemplary embodiments, chamber 304 may have one valve 306 for both nasal inserts 302. In other exemplary embodiments (not shown), chamber 304 may have one valve corresponding to each nasal insert 302. Chamber 304 may have a thinner top wall 308 disposed between the nasal inserts 302 to facilitate increasing the flexibility of chamber 304 so as to better conform to a patient's nostril configuration. In some exemplary embodiments, each nasal insert 302 may further have a flange 310 on the nasal aperture end 312 thereof.

Figure 4A:
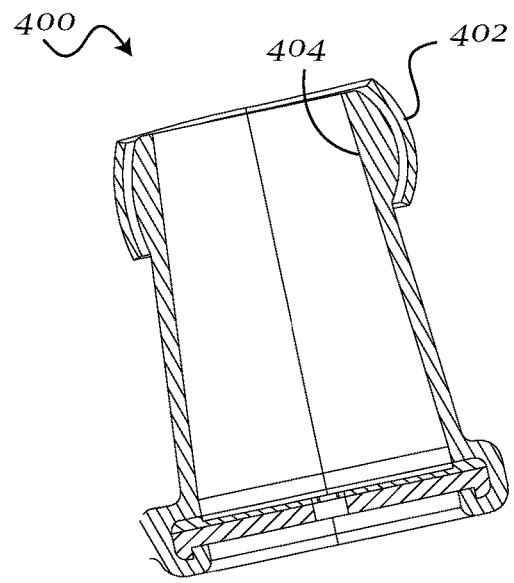
FIGS. 4A-4C illustrate additional exemplary embodiments of a nasal insert for a respiratory interface.
Figure 4B:
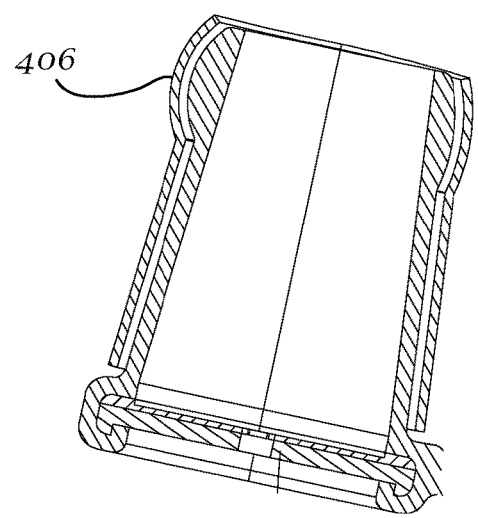
Figure 4C:
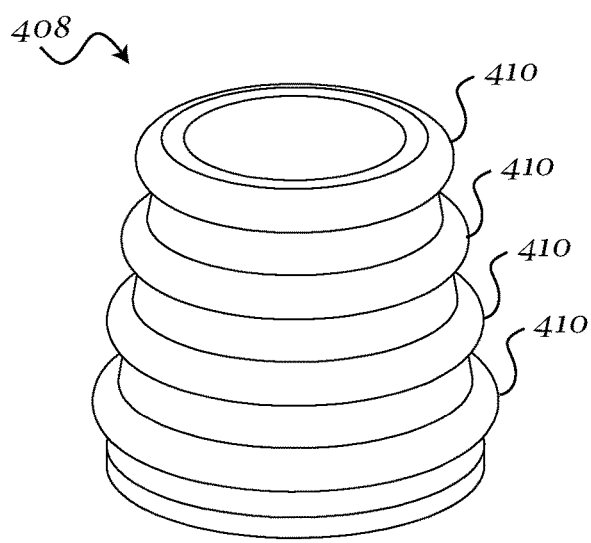

In some exemplary embodiments, multiple sizes of nasal inserts and/or flanges can be provided so as to allow for fitting different sizes of nostrils. The taper, shape, length, thickness, material, durometer, and other characteristics of a nasal insert and/or flange may be varied in design and construction as needed. FIG. 4A shows an exemplary embodiment of a nasal insert 400, where a second flange 402 may be coupled to nasal insert 400 over a first flange 404 so as to offer two different size configurations. FIG. 4B shows another exemplary embodiment of a nasal insert 400 having an outer nasal insert sleeve 406 coupled to nasal insert 400 so as to offer two different size configurations. A second flange 402 or an outer nasal insert sleeve 406 may be coupled to nasal insert 400 through any means known to one skilled in the art. FIG. 4C shows another exemplary embodiment of a nasal insert 408 having multiple flanges 410.

It should be understood that a valve may be incorporated into any of the embodiments described herein. An exemplary valve is described in the U.S. patent application Ser. No. 09/524,371, filed Mar. 13, 2000, now issued as U.S. Pat.

No. 6,478,026, which is hereby incorporated by reference in its entirety. The valve may allow air to pass through the nasal insert during inhalation, but may also work to prevent air from passing through the nasal insert during exhalation. The valve may serve to resist flow (i.e. increase resistance) in one direction. Increased resistance during exhalation may create a back pressure inside the patient's airway. In some exemplary embodiments, the valve may be replaceable. Features in the respiratory interface, such as ribs or walls, or separate components, such as the inlet aperture cover, may serve to limit or control the movement range of the valve.

Various valve types configured to allow gas passage in one direction can be utilized, e.g., a flapper valve, a check valve, a biased valve, a pucker valve, a duckbill valve, a dome valve, spring-loaded valve, propeller valve, shuttle valve, plunger valve, piston valve, or any other valve known in the art that enables the nasal interface to function as described herein. Valves that open when a certain pressure is reached (i.e. "cracking pressure") can also be utilized. Also, valves that have electronic adjustment can be utilized.

The embodiments disclosed herein may have at least one bleed port for expelling or exhausting gas. The bleed port may be of sufficient size and dimension to allow the patient's exhalation to exhaust from the interface. The bleed port can be located on any portion of the respiratory interface. For example, the bleeder port may be located at or proximate the valve or between the valve and the nasal aperture.

Various materials may be used to construct the respiratory interface. Exemplary materials for any of the components of the interface may include silicone, plastic, composite, or any material known to those of ordinary skill in the art. Some materials such as foams and gels may facilitate a design that could fit a wider range of nostrils. In some exemplary embodiments, the contact surface of the flange may have a silicone exterior and may be filled with gel or foam. In some exemplary embodiments, fabric may be used for at least a portion of the respiratory interface, for example for the chamber. In some exemplary embodiments, a portion of the respiratory interface could be inflatable or air-filled, for example the nasal insert.

Securing the respiratory interface may be accomplished in various ways. Securing the respiratory interface via the nasal insert shape, the materials, a flange, and/or headgear, have previously been described. Other ways of securing the respiratory interface, such as a over-nose strap, over-nose clip or spring, adhesive, septum clip or spring, or intra-nasal clip or spring, could alternatively be utilized.

While the embodiments described herein have been in the form of a nasal insert, it is envisioned that any style of interface could be combined with a valve. This can include, but isn't limited to, full-face masks, nasal masks, nasal prong interfaces, oral masks, and hybrid masks (i.e., combined masks such as an oral mask with nasal prongs or a nasal mask with nasal prongs). Exemplary masks are described in U.S. Patent Applications 2002/0059935 (now issued as U.S. Pat. No. 6,595,215), 2006/0124131 (now issued as U.S. Pat. No. 8,042,539), 2006/0174887 (now issued as U.S. Pat. No. 8,261,745), 2007/0221226 (now issued as U.S. Pat. No. 8,789,532), 2007/0272249 (now issued as U.S. Pat. No. 8,887,725), 2008/0011305 (now issued as U.S. Pat. No. 8,025,058), and 2009/0107506 (now expired), the disclosures of which are incorporated by reference herein in their entireties. As previously mentioned, the valve in larger interfaces may be improved if the valve is located substantially close to the patient's nose and/or mouth to minimize deadspace.

While embodiments described herein may be connected with a gas supply, mechanical ventilator, or PAP machine, the respiratory interface may function without being connected. The valve can allows the patient to generate the positive airway pressure needed for the treatment as previously described.

Several different methods may be envisioned to allow for evaluation of patient compliance with the respiratory interface. The respiratory interface may have a portion that changes color the longer the interface is used. The color change may result from wear, use, cleaning, and/or handling. The color change could result from contact with the patient or applied pressure (contact and/or gas). In some exemplary embodiments, the respiratory interface could have a portion that wears the longer the interface is used. The wear may result from use, cleaning, and/or handling. The wear could result from contact with the patient or applied pressure (contact and/or gas pressure). In some exemplary embodiments, a chemical reaction may occur when the respiratory interface is being used. For example, the chemical reaction may be activated by the applied pressure or by the humidity and/or temperature of the exhaled breath after a certain period of time that results in a color change or results in wear in a portion of the respiratory interface. The portion of the respiratory interface that is affected by the pressure, humidity, and/or temperature of the exhaled breath can be in the gas passageway between the nasal aperture and the inlet aperture.

The respiratory interface may include a sensor to allow for evaluation of patient compliance. The sensor may record strain, flow, or pressure. In one embodiment, a sensor (e.g. sensor 320) can be in the gas passageway between the nasal aperture and the inlet aperture for sensing gas flow or gas pressure (e.g. of the exhaled breath). The sensor may be removed from the respiratory interface for analysis. In some exemplary embodiments, the sensor may not be removed and the data may be collected by an external wired connection to the sensor or by wireless transmission.

A patient may need some time to adapt to breathing using a respiratory interface with a valve. The respiratory interface may be offered with different methods for adjusting the back pressure generated by the device. The respiratory interface may have different attachable/removable valves with different resistance values or performance. For example, the respiratory interface may have an adjustable or variable valve. The respiratory interface may have an adjustable or variable bleed port. The dimensions of the bleed port may affect the back pressure of the respiratory interface when the valve is closed. An exemplary variable bleed port is described in U.S. patent application Ser. No. 11/139,496, filed May 31, 2005, now issued as U.S. Pat. No. 7,559,327, which is hereby incorporated by reference in its entirety. An adjustable valve or adjustable bleed port may be adjusted manually or electronically. An adjustable valve or adjustable bleed port may self-adjust based on the respiratory interface sensing flow or pressure or may adjust based on a predetermined program. For example, an adjustable valve or adjustable bleed port may adjust based on a ramp time or the number of hours the respiratory interface is used. Power for an electronic valve or bleed port may come from one of the mentioned sources throughout.

The respiratory interface may include a method for generating, converting, capturing, returning, and/or recycling energy. Some of the materials and/or the design of the respiratory interface may have the ability to harvest energy. The respiratory interface may include small electronics, such as a processor, energy cells, batteries, transmitters, clock, etc. The respiratory interface may function to convert the exhaled breath, heat, and/or humidity into energy or pressure.

In one embodiment, the respiratory interface may create positive pressure in the patient's airway for at least a portion of the inhalation. The respiratory interface may capture energy from the patient's exhaled breath, via electrical, mechanical or other means and may return the energy to the patient in the form of pressurized air on the patient's inhale. This respiratory interface may have greater effect in treating sleep disordered breathing than an expiratory positive airway pressure (EPAP) only respiratory interface. By providing positive pressure support during at least a portion of the inhale, treatment could be improved. The respiratory interface could be passive (i.e. contain no powered electrical components). The respiratory interface could also be active and contain powered electrical components that can regulate pressure delivery. The energy could be captured by any of, but not limited to, the following: piezoelectric elements, elastomeric diaphragms, fan blades, elastomeric actuators, dielectric elastomers, and pneumatic actuators. The energy could be returned to the patient by any of the aforementioned means as well. It would be preferable but not required that the same element provide a means for capturing energy from the patient's exhaled breath and returning the energy to the patient in the form of pressurized air or other gas.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A respiratory interface for the treatment of breathing problems configured to be in flow communication with at least one of a user's nostrils, the respiratory interface comprising:
   at least one body with a gas passageway, wherein the at least one body has a sealing portion that is configured to contact the user's nose, a distal end configured to allow gas to enter the at least one body and a proximal end configured to allow gas to exit the at least one body into the at least one nostril of the user during inhalation, wherein the proximal end is configured to allow gas to enter the at least one body from the at least one nostril of the user and the distal end is configured to allow gas to exit the at least one body during exhalation;
   at least one nasal aperture at the proximal end of the at least one body; and
   at least one element coupled within the gas passageway between the distal end and the proximal end for evaluating when the respiratory interface has been used, wherein the respiratory interface is not connected to a gas supply during use for treatment, wherein the respiratory interface is configured to resist flow more during exhalation than during inhalation during use.

2. The respiratory interface of claim 1, wherein the at least one element is adapted to change color the longer the respiratory interface is used.

3. The respiratory interface of claim 1, wherein the at least one element is adapted to change color as a result of cleaning.

4. The respiratory interface of claim 1, wherein the at least one element is adapted to change color as a result of gas pressure.

5. The respiratory interface of claim 1, wherein the at least one element is adapted to change color as a result of a chemical reaction.

6. The respiratory interface of claim 1, wherein the at least one element is a sensor.

7. The respiratory interface of claim 1, further comprising at least one valve coupled to the at least one body.

8. The respiratory interface of claim 1, wherein the at least one element is adapted to change color as a result of humidity.

9. The respiratory interface of claim 1, wherein the at least one element is adapted to change color as a result of temperature.

10. The respiratory interface of claim 1, wherein the at least one element is adapted to change color as a result of the exhaled breath.

11. The respiratory interface of claim 1, wherein the at least one element is adapted to wear the longer the respiratory interface is used.

12. The respiratory interface of claim 1, wherein the at least one element is adapted to wear as a result of cleaning.

13. The respiratory interface of claim 1, wherein the at least one element is adapted to wear as a result of gas pressure.

14. The respiratory interface of claim 1, wherein the at least one element is adapted to wear as a result of a chemical reaction.

15. The respiratory interface of claim 1, wherein the at least one element is adapted to wear as a result of humidity.

16. The respiratory interface of claim 1, wherein the at least one element is adapted to wear as a result of temperature.

17. The respiratory interface of claim 1, wherein the at least one element is adapted to wear as a result of the exhaled breath.

18. A respiratory interface for the treatment of breathing problems configured to be in flow communication with at least one of a user's nostrils, the respiratory interface comprising:
   at least one body with a gas passageway, a distal end configured to allow gas to enter the at least one body and a proximal end configured to allow gas to exit the at least one body into the at least one nostril of the user during inhalation, wherein the proximal end is configured to allow gas to enter the at least one body from the at least one nostril of the user and the distal end is configured to allow gas to exit the at least one body during exhalation;
   at least one nasal aperture at the proximal end of the at least one body; and
   at least one sensor coupled within the gas passageway between the distal end and the proximal end, wherein the respiratory interface is not connected to a gas supply during use for treatment, wherein the respiratory interface is configured to resist flow more during exhalation than during inhalation during use.

19. The respiratory interface of claim 18, wherein the sensor is adapted to sense one of strain, flow, and pressure.

20. The respiratory interface of claim 18, wherein the sensor is removable.

21. The respiratory interface of claim 18, wherein the sensor is adapted to record data.

22. The respiratory interface of claim 18, further comprising at least one valve coupled to the at least one body.

* * * * *